United States Patent
Shahgaldian et al.

(10) Patent No.: US 8,871,837 B2
(45) Date of Patent: Oct. 28, 2014

(54) PREPARATION OF A MOLECULAR RECOGNITION ELEMENT

(75) Inventors: Patrick Shahgaldian, Saint Louis (FR); Alessandro Cumbo, Basel (CH); Philippe Corvini, Leymen (FR)

(73) Assignee: Fachhochschule Nordwestschweiz Hochschule fur Lifescience, Muttenz (CH)

( * ) Notice: Subject to any disclaimer, the term of this patent is extended or adjusted under 35 U.S.C. 154(b) by 50 days.

(21) Appl. No.: 13/823,304

(22) PCT Filed: Sep. 9, 2011

(86) PCT No.: PCT/EP2011/065671
§ 371 (c)(1),
(2), (4) Date: Mar. 14, 2013

(87) PCT Pub. No.: WO2012/034946
PCT Pub. Date: Mar. 22, 2012

(65) Prior Publication Data
US 2013/0184418 A1    Jul. 18, 2013

(30) Foreign Application Priority Data
Sep. 16, 2010   (EP) .................................... 10177028

(51) Int. Cl.
| | |
|---|---|
| *C08K 9/06* | (2006.01) |
| *B01J 20/26* | (2006.01) |
| *G01N 33/543* | (2006.01) |
| *C08G 77/18* | (2006.01) |

(52) U.S. Cl.
CPC .............. *C08G 77/18* (2013.01); *B01J 20/268* (2013.01); *G01N 33/54353* (2013.01); *G01N 33/54313* (2013.01); *G01N 2600/00* (2013.01)
USPC .............................................. 523/212; 435/4

(58) Field of Classification Search
CPC .............. B01J 20/268; G01N 2600/00; G01N 33/54353
USPC ................................................ 523/212; 435/4
See application file for complete search history.

(56) References Cited

U.S. PATENT DOCUMENTS

2004/0157209 A1\* 8/2004 Yilmaz et al. ..................... 435/5

FOREIGN PATENT DOCUMENTS

WO           01/19886          3/2001

OTHER PUBLICATIONS

International Preliminary Report on Patentability From the International Bureau of WIPO mailed Mar. 28, 2013 for PCT/EP2011/065671.

(Continued)

*Primary Examiner* — Kuo-Liang Peng
(74) *Attorney, Agent, or Firm* — Lowe Hauptman & Ham, LLP

(57) ABSTRACT

A method for preparation of a molecular recognition element comprising the steps of binding a template to a surface of a carrier material, providing a recognition material to the surface of the carrier material, initiating polymerization of the recognition material on the surface of the carrier material, stopping the polymerization of the recognition material on the surface of the carrier material, and releasing the template from the surface of the carrier material and the polymerized recognition material. The method is characterized as an aim size of individual imprints is predefined, and the polymerization of the recognition material on the surface of the carrier material is stopped when a size of individual imprints of the polymerized recognition material essentially equals the predefined aim size. This method is readily applicable for preparation of a molecular recognition element useful as a drug, catalyst, competitive affinity ligand inhibitor, competitor, agonist, antagonist or diagnostic agent.

13 Claims, 7 Drawing Sheets

(56) References Cited

OTHER PUBLICATIONS

S. Blasenbrey et al., Macromolecular Colloquium, Lecture, Mar. 2-4, 1972, 334-342pages, vol. 11 (1972) at Freiburg/Br.(Germany).

Toru Shiomi et al., A method for the molecular imprinting of hemoglobin on silica surfaces using silanes, Article, Feb. 8, 2005, 8pages, Science@Direct.

Birnbaumer Gerald M. et al.;"Detection of viruses with molecularly imprinted polymers integrated on a microfluidic biochip using contact-less dielectric microsensors"; Lab on a Chip, vol. 9, No. 24; Oct. 12, 2009; pp. 3549-3556.

Dickert Franz L. et al.;"Bioimprinted QCM sensors for virus detection-screening of plant sap"; Analytical and Bioanalytical Chemistry; vol. 378, No. 8; Apr. 2004; pp. 1929-1934; ISSN: 1618-2642.

Bolisay Linden D. et al.; "Optimization of Virus Imprinting Methods to Improve Selectivity and Reduce Nonspecific Binding"; Biomacromolecules; vol. 8, No. 12; Nov. 14, 2007; pp. 3893-3899; ISSN: 1525-7797.

International Search Report mailed Dec. 6, 2011 for PCT/EP2011/065671, citing the above reference(s).

Written Opinion From the ISA mailed Dec. 6, 2011 for PCT/EP2011/065671, citing the above reference(s).

* cited by examiner

PREPARATION OF A MOLECULAR RECOGNITION ELEMENT

CROSS REFERENCE TO RELATED APPLICATION

This application claims the priority of European Patent Application No. 10177028.7, filed on Sep. 16, 2010 in the EPO (European Patent Office). Further, this application is the National Phase application of International Application No. PCT/EP2011/065671 filed Sep. 9, 2011, which designates the United States and was published in English.

TECHNICAL FIELD

The present invention relates to a method according to the preamble of independent claim 1. Such a method comprising binding a template to a surface of a carrier material, providing a recognition material to the surface of the carrier material, initiating polymerization of the recognition material on the surface of the carrier material, stopping the polymerization of the recognition material on the surface of the carrier material, and releasing the template from the surface of the carrier material and the polymerized recognition material can be used for preparation of a molecular recognition element useful as a drug, catalyst, competitive affinity ligand inhibitor, competitor, agonist, antagonist or diagnostic agent.

BACKGROUND ART

Molecular recognition is a pillar of modern biomolecular sciences because of its ubiquitous involvement in biochemical processes. Among the large variety of synthetic receptors developed to mimic natural systems and used for their capabilities of molecular recognition, molecularly imprinted organic materials are attracting an increasing interest because of their versatility and almost unlimited possibilities. Molecular imprinting is a technique for synthesizing polymers (molecularly imprinted polymers (MIPs)) using a template (e.g. polypeptides, proteins, bacteria or low molecular weight compounds) with specific binding sites, whereby monomers are polymerized in the presence of the template. The synthesized polymer then possesses molecular recognition properties for a target being complementary to the template. The MIPs adopt a structure containing recognition imprints (imprints) where binding-functions capable of chemical interactions with the target are specifically oriented by interaction with the template. When the template is washed-off, the binding-functions per imprint are conserved. The so-produced MIPs have been demonstrated to possess enhanced molecular recognition properties for the target, and thus, serve as a polymerized recognition material or element.

Molecular imprinting has been described, for example, by Wulff et al. but its development was hindered at the early stage by tedious experimental protocols (Wulff et al., Angew. Chem. Int. Ed. Engl., 1972, 11, 341). Improvement and optimizations have led to more developed and applicable systems compatible with commercial applications. Two different imprinting approaches are known in the art: the first one consists in grafting covalently a target to the polymer-forming building blocks such as monomers while the second approach is based on the non-covalent interactions of a template with monomers.

A main limitation of methods described in the art is a limited availability of binding-functions of a polymerized recognition material. Indeed, bulk-polymerization of monomers around a template causes a formation of the binding-functions inside a so-formed polymer thus limiting an application to target molecules which can diffuse inside a polymer (size and solubility limitation) and to inexpensive targets.

Different approaches have been proposed to circumvent this limitation including creating imprints only at a surface of a polymer, thus forming a polymerized recognition material. One approach is explored based on a growth of a monomolecular layer on a surface where a template is immobilized. After growth of the monomolecular layer on the surface, the template is removed from the surface and, thus, a so-formed molecular recognition element can be used for molecular recognition of a target. However, this approach is limited to small molecules because of limited thickness (i.e. in a range of 1 to 2 nm) of the monomolecular layer as polymerized recognition material of the molecular recognition element. Another approach known in the art is described by Shiomi et al. (Biomaterials 2005, 26, 5564-5571) and relates to a preparation of a molecular recognition element for a target (e.g. protein) by molecular imprinting using a covalently immobilized template on a silica surface, onto which silane polymerization was performed in order to generate a polymerized recognition material. Within this method, hemoglobin (Hb) has been employed as template protein for creating Hb-specific imprints on the silica surface. However, this method is pretty limited and not applicable to a larger supramolecular complex, e.g. virus. Moreover, it does not allow controlling of degree of affinity of the polymerized recognition material of the molecular recognition element for its target.

There is therefore an unmet need for a method providing a molecular recognition element, wherein a control and adjustment of specificity and affinity for binding targets such as small targets with low molecular weight or particularly of complex targets with high molecular weight to a polymerized recognition material of the molecular recognition element is enabled.

DISCLOSURE OF THE INVENTION

According to the invention this need is settled by a method of preparation of a molecular recognition element as defined by the features of independent claim 1. Preferred embodiments are subject of the dependent claims.

In particular, the present invention provides a method for preparation of a molecular recognition element comprising the steps of binding a template to a surface of a carrier material, providing a recognition material to the surface of the carrier material, initiating polymerization of the recognition material on the surface of the carrier material, stopping the polymerization of the recognition material on the surface of the carrier material, and releasing the template from the surface of the carrier material and the polymerized recognition material. Further, an aim size, of individual imprints is predefined and the polymerization of the recognition material on the surface of the carrier material is stopped when a size of individual imprints of the polymerized recognition material essentially equals to the predefined aim size.

As used herein, recognition material relates to a material being capable to a polymerization reaction which material can be provided to the surface of the carrier material. Preferably, the recognition material is a monomeric material having affinity for a part of the template and is provided in liquid phase. During polymerization, the recognition material can self-assemble around the template and is included in a recognition layer grown from the surface of the carrier material into direction of the template or from the template into direction of the surface of the carrier material or both. After being polymerized, the recognition material usually is in solid phase.

Applying the method according to the invention, the polymerized recognition material has a structure comprising the homogeneous imprints formed by the template. Within the imprints, there may be binding-functions being specifically oriented by interaction with the template, which are capable of chemical interactions with a target. Thus, the polymerized recognition material is capable of molecular or biomolecular recognition of targets such as supramolecular complexes, viruses, nucleic acids, peptides, proteins, polymeric nanoparticles, inorganic nanoparticles, prokaryotic cells, eukaryotic cells, plant cells and derivatives thereof. The template may be selected in accordance with a target to which the molecular recognition element is to be applied. When the template or the target has a known structure (e.g. a virus) chemical functions of a surface of the template and/or of the target may be identified. In particular, the template can be identical to the target, such as for example the same virus which is intended to be trapped by the molecular recognition element can be used as template for creating the molecular recognition element.

The term "imprint", as used herein, relates to a cavity formed by the template during polymerization of the recognition material. Particularly, by releasing the template from the polymerized recognition material the imprint is formed in the polymerized recognition material, being complementary to a target. Within the imprint, there may be binding-functions, which are capable of chemical interactions with the target and which are specifically oriented by interaction with the template.

A preferred polymerization within the inventive method can be based on a poly-condensation of silica precursors such as tri-alkoxy-silane and tetra-alkoxy-silane under aqueous conditions. An alternative possible polymerization can be radical polymerization using surface bound or soluble initiator, water soluble unsaturated monomers or water soluble cross-linker. Further, stopping the polymerization of the recognition material on the surface of the carrier material can be performed by actively stopping the polymerization reaction or by self-stopping of the polymerization reaction.

The method according to the invention allows for producing all the binding-functions within the imprints being fully accessible by the target and in particular not limited by a diffusion rate of the target within the polymerized recognition material. Further, it allows for precisely adjusting the size of the imprints and therefore for providing a predefined amount of binding-functions per imprint. Thus, the affinity and specificity of the molecular recognition element for the target can be controlled and tuned depending on the intended application of the molecular recognition element. Also, the binding of the template only at the surface of the carrier material enables a decrease of the amount of template needed for the preparation process which may be a crucial asset for preparing molecular recognition elements for expensive and/or rare targets such as, e.g., viruses.

Preferably, predefining the aim size comprises predefining an aim thickness, wherein the polymerization of the recognition material on the surface of the carrier material is stopped when a thickness of the polymerized recognition material essentially equals to the predefined aim thickness. By controlling the thickness of the polymerized recognition material, the size of the individual imprints and therefore the affinity of the polymerized recognition material for the target can conveniently be adjusted and optimized for an intended application. For example, increasing the thickness of the polymerized recognition material may result in an increase of the number of binding-functions per imprint being formed by means of the template in the polymerized recognition material, such that the selectivity and, thus, the specific affinity of the polymerized recognition material with regard to the target is increased.

Particularly, by controlling the thickness, the growth of the polymerized recognition material may be controlled and adjusted in a range from 1 to 500 nm, 1 nm to 450 nm, 1 nm to 400 nm, 1 nm to 350 nm, 1 nm to 300 nm, 1 nm to 250 nm, preferably 1 nm to 200 nm. Within these ranges, an accuracy level of the growth of the polymerized recognition material may be in a range from 1 to 10 nm, from 1 nm to 5 nm, from 1 nm to 4 nm, from 1 nm to 3 nm, from 1 nm to 2 nm, preferably 1 nm. The thickness may be checked using a microscope such as scanning electron microscope (SEM), transmission electron microscopy (TEM), scanning probe microscopy (SPM) or light scattering methods. For example, as it is known in the art, SEM is a type of electron microscope that images a surface of a sample by scanning it with a high-energy beam of electrons in a raster scan pattern. The electrons interact with the atoms that make up the sample producing signals that contain information about the surface's topography (e.g. topography of polymerized recognition material), composition and other properties such as electrical conductivity. The way for carrying out such a kind of microscopy for analysis purpose is well known to the skilled person.

Stopping the polymerization of the recognition material on the surface of the carrier material, when a thickness of the polymerized recognition material essentially equals to the predefined aim thickness, allows for a precise control of the size of the individual imprints and thus of the number of binding-functions per imprint in the polymerized recognition material. Like this, affinity and specificity of the molecular recognition element for its target can be precisely controlled and tuned. In this context, also a growth kinetic of the polymerized recognition material comprising thickness of the recognition material to be polymerized for given conditions may be preliminary determined. The results of the determination may be then used to stop the polymerization after essentially equalizing the predefined aim thickness of the polymerized recognition material.

Preferably, predefining the aim thickness comprises predefining an aim polymerization duration under given conditions and the polymerization of the recognition material on the surface of the carrier material is performed under the given conditions and stopped when a duration of the polymerization of the recognition material on the surface of the carrier material essentially equals to the predefined aim polymerization duration. The term "conditions" in this context relates to parameters of which a growth of the recognition material is dependent. In particular, it may relate to the concentration and composition of the monomers used in the recognition material, the polymerization temperature, pressure and/or humidity.

Such a stopping of the polymerization of the recognition material allows a precise control of the thickness of the polymerized recognition material, thus of the size of the individual imprints and thus of the number of binding-functions per imprint in the polymerized recognition material. Like this, affinity and specificity of the molecular recognition element for its target can be precisely controlled and tuned. Based on control of the aim thickness, the number of binding-functions per imprint on the polymerized recognition material may be set, whereby affinity and specificity of the polymerized recognition material for its target is controlled and tuned. In this context, a growth kinetic of the polymerized recognition material comprising polymerization duration of the recognition material to be polymerized for given conditions may be preliminary determined. The results of the determination may then be used to stop the polymerization after essentially equalizing the predefined aim polymerization duration.

Preferably, the template is a virus or a structural analogue of a virus and the aim thickness is within a range of about 1% to about 50% of a diameter of the template, or optionally about 45% to about 50% of a diameter of the template, or optionally about 47% to about 50% of a diameter of the template, or optionally about 48% to about 50% of a diameter of the template, or optionally about 49% to about 50% of a diameter of the template. The term structural analogue of a virus, as used herein, relates to objects having an analogue structure and/or morphology as a virus such as synthetic nanoparticles. Preferably, the degree of analogy between the virus and its analogue may be within a range of about 90% to 100%, preferably 90%, 91%, 92%, 93%, 94%, 95%, 96%, 97%, 98%, 99% or 100%. The term "about" in this context particularly relates to a dimension being exactly a respective diameter of a virus or a few nanometers less than the respective diameter of the virus, such as about 1 nm less, about 2 nm less, about 3 nm less, about 4 nm less or about 5 nm less.

Since viruses often have a more or less spherical shape, providing a polymerized recognition material of a thickness of more than half of the diameter of the virus could hinder the release of the template from the polymerized recognition material. Further, even though providing a rather thin polymerized recognition material would allow an easy release of the template, imprints with comparably few binding-functions would only be generated. Thus, establishing a polymerized recognition layer with a thickness which is slightly smaller than half of the diameter of the virus allows for a convenient provision of a recognition element with a high affinity for the virus.

Preferably, predefining the aim size comprises predefining an aim polymerization duration under given conditions wherein the polymerization of the recognition material on the surface of the carrier material is performed under the given conditions and stopped when a duration of the polymerization of the recognition material on the surface of the carrier material essentially equals the predefined aim polymerization duration. Such a stopping of the polymerization of the recognition material allows for a precise control of the polymerization duration, thus of the thickness of the polymerized recognition material, thus of the size of the individual imprints and thus of the number of binding-functions per imprint in the polymerized recognition material. Like this, affinity and specificity of the molecular recognition element for its target can be conveniently controlled and tuned. In this context, a growth kinetic of the polymerized recognition material comprising polymerization duration of the recognition material to be polymerized for given conditions may be preliminary determined. The results of the determination may be used to stop the polymerization after essentially equalizing the predefined aim polymerization duration.

Preferably, the method according to the invention comprises the step of activating the surface of the carrier material prior to binding the template to the surface of the carrier material, wherein a linking means is homogeneously distributed on the surface of the carrier material. In this context, the homogeneous distribution of the linking means relates to the linking means being bound on the surface of the carrier material by equal spacing between them. Homogeneity of binding sites presented by linking means may depend on homogeneity of the surface of the carrier material and/or symmetry of the template.

As used herein, the term "linking means" relates, e.g., to cross-linking reagents or cross-linkers containing reactive ends to specific functional groups (e.g. primary amines, sulfhydryls, etc.) which bind on one side to the surface of the carrier material and on the other side to a template. Cross-linkers may be used to modify nucleic acids, proteins, polymers and solid surfaces or solid templates. For example, a cross-linker may be immobilized on a silica surface as a carrier material and then a template may be bound to an unoccupied binding-site of the cross-linker. Alternatively, the cross-linker may firstly bind to the template and then the cross-linker bound by the template may bind with its unoccupied binding-site to the silica surface. The cross-linker used within the method according to the present invention may depend on type of carrier material to be used such as inorganic oxides such as silicon oxides or titanium oxides, organic, inorganic, polymeric or inorganic-organic composites and self-assembled organic material. Preferably, the cross-linker may be a cleavable cross-linker, i.e. a cross-linker being capable to cleave its linkage upon external stimuli such as temperature, pH, electricity, light, or a cross-linker such as DTSSP (3,3'-Dithiobis[sulfosuccinimidylpropionate]) being cleavable, for example, by using DTT (Dithiothreitol) as a reducing agent. As a non-limiting example, an amino-modified silica surface as a carrier material may be modified with a homo-bifunctional cross-linker (e.g. glutaraldehyde) forming a Schiff base with the amine group at the surface of the carrier material. The remaining free aldehyde group can then form another Schiff base with the template, and, thus, the template can be linked at the surface of the carrier material. The template can be released in acidic conditions. In case of gold or titan surface as a carrier material, a cross-linker may have a thiol terminus enabling binding to the respective surface and further an intramolecular disulfide bond being cleavable and may link the respective surface with the template. As used herein, cross-linkers are versatile and can be applied to any kind of carrier material, as long as it possesses the appropriate chemical functions. As a non-limiting example, the following list summarizes different cleavable amino reactive cross-linkers modifying carrier material which can be used within the method according to the present invention:

EGS (Ethylene glycol bis[succinimidylsuccinate]), cleavable with hydroxylamine

Sulfo-EGS (Ethylene glycol bis[sulfosuccinimidylsuccinate]), cleavable with hydroxylamine BSOCOES (Bis[2-(succinimidooxycarbonyloxy)ethyl] sulfone), cleavable with a base DSP (Dithiobis[succinimidyl propionate]), cleavable with a thiol DTSSP (3,3'-Dithiobis[sulfosuccinimidylpropionate]), cleavable with a thiol DTBP (Dimethyl 3,3"-dithiobispropionimidate-2 HCl), cleavable with a thiol DST (Disuccinimidyl tartarate), cleavable with peridoate Cross-linkers are also available for cross-linking amine to sulfhydryl (thiol) functions, Sulfo-LC-SMPT (4-Sulfosuccinimidyl-6-methyl-a-(2-pyridyldithio)toluamido]hexanoate)), cleavable with a thiol SPDP (N-Succinimidyl 3-(2-pyridyldithio)-propionate), cleavable with a thiol LC-SPDP (Succinimidyl 6-(3-[2-pyridyldithio]-propionamido)hexanoate), cleavable with a thiol SMPT (4-Succinimidyloxycarbonyl-methyl-a-[2-pyridyldithio]toluene), cleavable with a thiol Cross-linkers are also available for cross-linking sulhydryl to sulfhydryl (thiol) functions DPDPB (1,4-Di-[3'-(2'-pyridyldithio)-propionamido]butane), cleavable with a thiol DTME (Dithio-bismaleimidoethane), cleavable with a thiol BMDB (1,4 bismaleimidyl-2,3-dihydroxybutane), cleavable with periodate.

Preferably, the linking means is homogeneously distributed on the surface of the carrier material due to a patterned surface of the carder material. Particularly, the patterned surface of the carrier material can be complementary to a shape of the template. The patterned surface may be obtained in various ways such as preparing a surface being composed of particles, i.e., nanoparticles, wherein each particle has a predefined diameter. Further, a patterned surface may be obtained by structuring the surface with attractant and non-attractant areas being homogenously distributed on the surface of the carrier material. The attractant areas, for example, have an affinity to a linking mean. In contrast, the non-attractant areas have reduced or no affinity to the linking means and thus the linking means is not able to bind to the surface of the carrier material. Such structured surfaces may be obtained by well known technique, e.g. photolithographic approach or microcontact-printing.

Preferably, the method according to the invention comprises the step of providing building blocks complementary to the template prior initiating polymerization of the recognition material on the surface of the carrier material.

If the template and/or the target have/has a known structure (e.g. virus), chemical functions of the surface of template or target can be identified. Thus, selection of building blocks used to prepare the recognition material may be dependent on the known structure of the template and/or target in order to adapt the affinity of the recognition material. Alternatively, the building blocks can also be provided to the template independently from recognition material, e.g., prior providing the recognition material. This step enables self-assembly of the building blocks to the template and defines specificity of the recognition material in order to be capable for a specific binding of its template or target. The choice of the building blocks which can be used to prepare the recognition material may depend on the known structure of the template or the target in order to adapt the affinity of the recognition material to its respective need. The composition of the recognition material depends on reaction mixtures such as structural building blocks (e.g. tetraethylorthosilicate (TEOS)) and/or recognition building blocks (e.g. tetraethylorthosilicate (TEOS), 3-Aminopropyltriethoxysilane (APTES), n-Propyl-triethyoxysilane (PTES), Isobutyltriethoxysilane (IBTES), Hydroxymethyltriethoxysilane (HTMEOS), Benzyltrielthoxysilane (BTES), Ureidopropyltriethoxysilane (UPTES), Carboxyethyltriethoxysilane (CETES)) and a self preorganizing of these building blocks around the template via weak force interactions such as hydrogen bonding, electrostatic interactions, hydrophobic interactions or van-der-Waals interactions, $\pi$-$\pi$ stacking.

Preferably, the method according to the invention comprises the steps of analysing a surface structure of the template or of a target prior providing the building blocks, and choosing the building blocks corresponding to the surface structure. This step can be useful for enabling a specific binding of the template/target to the recognition material, particularly if the template and/or the target has a known structure as mentioned above.

Preferably, an outer surface of the polymerized recognition material being opposed to the carrier material is passivated prior the template being released from the surface of the carrier material and the polymerized recognition material, Such passivation can be performed in order to change the chemical properties of the outer surface such as to decrease the unspecific interaction of the outer surface. As used herein, "unspecific interaction" relates to weak force interactions possibly occurring between the outer surface of the polymerized recognition material and molecules unspecific adsorbing to this surface. These weak force interactions may be hydrogen bonding, electrostatic interactions, hydrophobic interactions or van-der-Waals interactions, $\pi$-$\pi$ stacking. This allows increasing the selectivity of the recognition element for the target. Preferably, passivating the outer surface of the polymerized recognition material comprises chemical and/or physical and/or biochemical modification of the outer surface of the polymerized recognition material on the surface of the carrier material. Such passivation can also be useful to decrease unspecific interaction properties of the outer surface of the polymerized recognition material weak force interactions.

Preferably, releasing the template from the surface of the carrier material and the polymerized recognition material comprises breaking the binding between the template and the carrier material without impairing the template. With such a step, a gentle release of the template can be enabled and thus the released template may be reused for preparation of a further molecular recognition element. This can be particularly suitable for expensive and/or rare template materials. Such a gentle release of the template may be achieved by breaking the binding between the template and the carrier material which may be accomplished by using reversible chemical reactions such as breaking of a Schiff base using acidic treatment, reduction or oxidation of disulfide bond, or using cleavable cross-linkers, i.e. OTSSP (3,3'-Dithiobis[sulfosuccinimidylpropionate]) being, cleavable, for example, by using (Dithiothreitol) as a reducing agent.

Preferably, the binding of the template to the surface of the carrier, material is covalent binding. A covalent binding of the template within the method according to the present invention contributes to strong-bound template to the surface of the carrier material. Thus, a covalently bound template contributes to a stable surface of the carrier material bearing the templates which may provides stable conditions for polymerization of the recognition material.

Preferably, the template is selected from a group consisting of supramolecular complexes, viruses, nucleic acids, peptides, proteins, polymeric nanoparticles, inorganic nanoparticles, prokaryotic cells, eukaryotic cells, plant cells and derivatives thereof.

Preferably, the carrier material is selected from a group consisting of inorganic oxides such as silicium oxides or titanium oxides, organic, inorganic, polymeric or inorganic-organic composites and self-assembled organic material. For example, the carrier material can be a surface layer of a chip or a drug or the like.

Preferably, the carrier material is a silicium oxide surface. In case, the silica surface is composed of particles, one template per particle may be bound, provided that particle size, i.e. diameter, corresponds to template size. Alternatively more templates per particle may be bound, depending on ratio of particle size to template size. Preferably, there are about 200 imprints per nanoparticle.

In a further aspect of the present invention, a pharmaceutical composition comprises a recognition element prepared by the method according to the present invention for use in treating a disease, disorder or condition or symptoms of said disease selected from viral infections and cancer.

In another further aspect of the present invention, use of a recognition element prepared by the method according to the present invention is envisaged for the preparation of a pharmaceutical composition for treating a disease, disorder or condition or symptoms of said disease selected from viral infections and cancer.

Like this, the disease, disorder or condition or symptoms of said disease such as viral infections and/or cancer may be efficiently treated using the recognition element obtained by the method according to the present invention. For example, the molecular recognition element obtained by the method described above may be part of the formulation of cream designed to the treatment viral skin infections via topical application (e.g. Measles, Chickenpox, Rubella). The presence of molecular recognition element may allow the retention of the viral particles and strengthen the efficacy of the therapeutic pharmaceuticals. Thus, the present invention may be used for purification of viruses within the therapeutic treatment.

In another further aspect of the present invention, use of a recognition element prepared by the method according to the present invention is envisaged for identification, purification or analysis of biomacromolecules, medical diagnosis, genetic therapy, cleaning products, health care devices, protective equipment and warning system, food industry, agricultural or environmental application.

The method according to the present invention can be broadly applied and may be particularly useful in the field of analysis such as purification of antibodies, i.e., production of material for the purification of antibodies for the production of vaccines against viral diseases. Subsequent to immunization, the mono/polyclonal antibodies contained in the bulk extract could be applied to packed-beds consisting of imprinted materials. Adequate buffers for application and elution steps will enable the recovery of affinity-purified antibodies.

The present invention further may be used in medical diagnostics to quickly detect and identify viral infections. A chromophore might be embedded in the recognition layer during its synthesis and successively turn in a colorimetric signal upon binding with target virus. Such quick diagnostics tool would be used as portable kit. Virus imprinted particles (VIPs) can be immobilized at the surface of a sensor device (e.g. quartz crystal microbalance, surface plasmon resonance) or in a microtiter plate and used for diagnostic applications.

Further, genetic therapies using viral vectors may be a further application of the present invention, e.g. controlled release or recapture of viruses used to shuttle genes. In a formulation, the VIPs, pre-loaded with relevant viral species, can be used to deliver in a controlled way those viruses (i.e. containing the genes to be transfected in the defective cells) Conversely the recognition material may be applied to the patient to "re-capture" remaining viruses that have been previously used to shuttle genes in order to prevent from possible side-effect viral contamination caused by virus-based genetic therapy.

The method according to the present invention can also be particularly useful in the field of pharmaceutical industry, e.g. therapeutic treatments: ingredient for a formulation of therapeutic pharmaceuticals for a treatment of viral diseases. The molecular recognition element obtained by the method according to the present invention may be part of the formulation of cream designed to the treatment viral skin infections via topical application (e.g. Measles, Chickenpox, Rubella). The presence of molecular recognition element may allow the retention of the viral particles and strengthen the efficacy of the therapeutic pharmaceuticals. Thus, the present invention may be used for purification of viruses. The present invention may also be applied to anti-viral treatment and chirurgical applications, e.g. selective elimination of viruses. Prior to the administration of recognition material to the patient, modifications of the recognition material through coating/binding of antiviral drugs (e.g. Zidovudine (AZT)) may enable the selective killing of viruses, which may bind to the recognition material.

Moreover, the present invention may be applicable to separation techniques, e.g. production of material for chromatographic applications to purify strain of viruses. The packing of recognition materials in column may be performed in order to retain/purify specifically the virus of interest when present in mixture of viruses or complex biological extracts in research and development laboratories.

The present invention is also applicable to personal care products/household and industrial cleaning products, e.g. antiviral healthcare/personal care products such as anti-viral lotions, soap and creams, e.g. ointments against herpes simplex virus. A non-limiting example may be an addition of the recognition material by formulating salve with anti proliferative properties for local application treatment against e.g. herpes simplex virus or zona virus.

Formulation of cleaning/disinfecting products for households and public buildings and transportation means may be also realized by the method of the present invention. The application may be consist in the addition of the recognition material in the formulation of the above cited household cleaning/disinfecting products.

The present invention is further applicable to protective equipment and warning system applications, e.g. warning systems for contamination of drinking water tanks and pipelines (e.g. terrorist attacks). The recognition material may be immobilized/coated/embedded in various sensing layers of probes, which are connected to signal transducers. Storage tanks and facilities used for the production of consumable water can be equipped with such sensor-based warning systems to prevent the use of this water in case of biological terrorism attack. The described systems could be used as warning systems to prevent contamination of industrial or production lines (food, pharmaceuticals, environmental treatment, etc.).

Also, warning systems for release of viruses out of laboratories may be realized by the use of the present invention. Materials recognizing specifically viruses handled in Biosafety levels 3 and 4 laboratories may be used for the production of sensors, which are embedded for instance in the filters treating air in such facilities. Similar sensors may be used for warning systems to detect presence of air-borne viruses in aeration, warming and cooling systems.

However, other industrial processes such as food industry may apply the present invention, e.g. production of recognition material specific for viruses can be used in the food industry (e.g. dairy or other fermentation processes sensible to bacteriophages). They may be used for the preparation of packed column, the immobilization to further material, e.g. filtration membranes, or as powdered formulations to capture the undesired viruses.

Further, molecular biology applications may be realized by the present invention where viruses or other cell/molecule material is required. When the genetic material of specific viruses is necessary purification columns can be prepared using the recognition material.

However, the present invention is applicable to personal healthcare devices such as anti-viral protection masks and equipment. A possible application of the recognition material is its use for the direct coating of protection masks. For masks equipped of air cartridge filters, the embedment of the material in the cartridge is envisaged. The recognition material may be used for the production of protective equipments for army in case of bioterrorism. This may be achieved by means of usual coating, deposition, copolymerization technologies used in the textile industry.

Further application of the present invention are personal diagnostic applications, for instance to determine for coming outbreak of viral infections, e.g. herpes simplex virus (HSV). A possible application may be the embedment of the recognition material in kits which supply information on the process of breaking out infections. Such kits may be based on cheap technologies such as calorimetry.

Another application of the present invention may be agricultural/veterinary and gardening applications such as pesticide, e.g. the recognition material may be used as an ingredient for the formulation of preventive and curative anti-viral pesticides/therapeutic agents for animal breeding, aquaculture and agriculture; diagnostic application, e.g. production of kits and devices for the diagnostic. The recognition material may be used in the form of microplate-based detection kits or probes for diagnostic viral diseases for vegetal, cattle and fishes. Possible detection principles may rely on colorimetry, spectrophotometry and -fluorometry; treatment/sensing technologies, e.g. relying on the use of the recognition material may be applied to for diagnostic of viral contamination of installations used for the production of vegetals, aquaculture and cattle breeding.

The present invention may also be applicable to environmental applications such as wastewater treatment, e.g. material to remove viral contaminants during the treatment of wastewater. The recognition material can be directly used for the preparation of packed-bed reactor systems to treat water via a percolation process. A further possible technology is the immobilization/embedment of these recognition materials in filtration membranes treating effluents. A more simple application is the direct use of the recognition material as a suspension of fine powder in cleaned wastewater to capture the viruses in systems retaining the particles. The above cited systems may be used to prepare virus-free during the reclaiming/recycling of treated sewage water. These technologies may also be used to remove viral contaminants during the production of drinking water. This application may be seen in the format of filter for the depuration of domestic water, which may be relevant in developing country.

In another further aspect of the present invention, use of a recognition element prepared by the method according to the present invention as drug, catalyst, competitive affinity ligand inhibitor, competitor, agonist, antagonist, or diagnostic agent is envisaged.

These and other aspects of the invention will be apparent from and elucidated with reference to the embedment(s) described hereinafter.

BRIEF DESCRIPTION OF THE DRAWING

The method according to the invention is described in more detail herein below by way of exemplary embodiments and with reference to the attached drawings, in which:

FIG. 3 shows a scanning electron micrograph of virus imprinted particles (VIPs) which comprise the SNPs from FIG. 1 as a molecular recognition element provided by the embodiment of the method according to the invention;

FIG. 4 shows a SDS-PAGE (sodium dodecylsulfate polyacrylamide gel electrophoresis) representing an interaction assay for analysing a VIPs-target interaction compared to a non-imprinted particles (NIPs) target interaction wherein the VIPs are the molecular recognition element from FIG. 3;

DETAILED DESCRIPTION OF THE PRESENT INVENTION AND PREFERRED EMBODIMENTS

Figure 1:
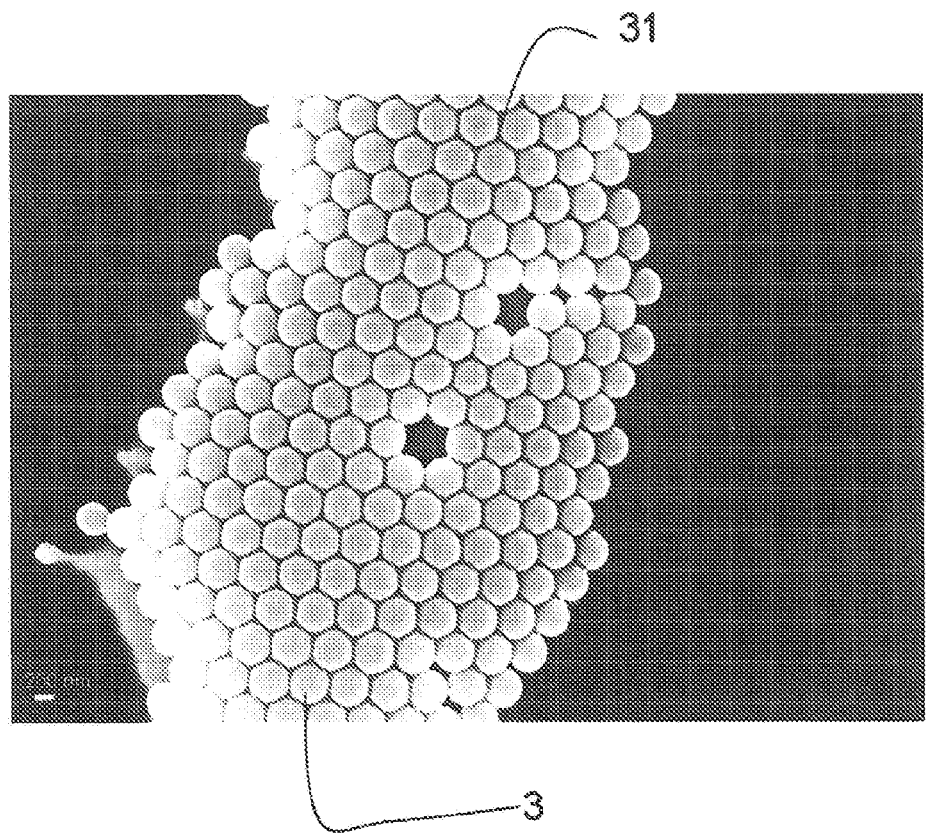
FIG. 1 shows a scanning electron micrograph of silica nanoparticles (SNPs) as a carrier material within an embodiment of the method according to the invention.

FIG. 1 shows a scanning electron micrograph of silica nanoparticles (SNPs) 3 usable as a carrier material within an embodiment of the method according to the present invention. The SNPs 3 may be essentially monodisperse, wherein each single SNP 3 may have a defined size in a range of 20 nm to several μm, e.g. about 400 nm as shown in FIG. 1.

Figure 2:
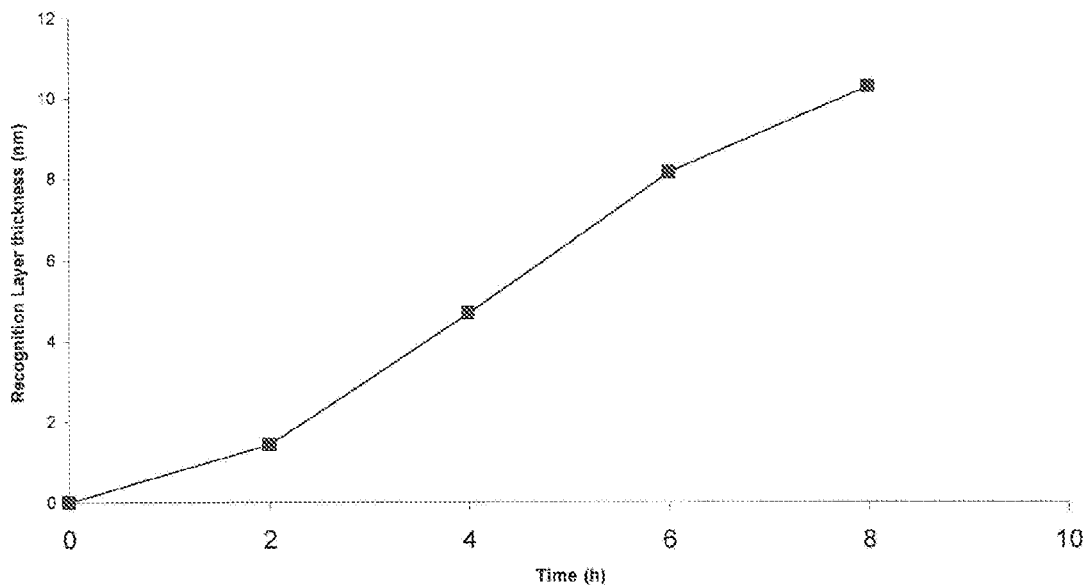
FIG. 2 shows time-dependently measured layer thickness of a recognition material polymerized on a surface of a carrier material.

FIG. 2 shows time-dependently measured layer thickness of a polymerized recognition material according to the present invention wherein a TYMV (turnip yellow mosaic virus) has been used as template. For example, if the thickness of the polymerized recognition material is comparably low such as 2 nm, then polymerization duration is about 2 h. For a higher thickness (for example 10 nm) of the polymerized recognition material, the polymerization duration is about 8 h. Thus, it is possible to exactly predefine an aim thickness of the polymerized recognition material by predefining a duration of polymerization.

Figures 3, 4:
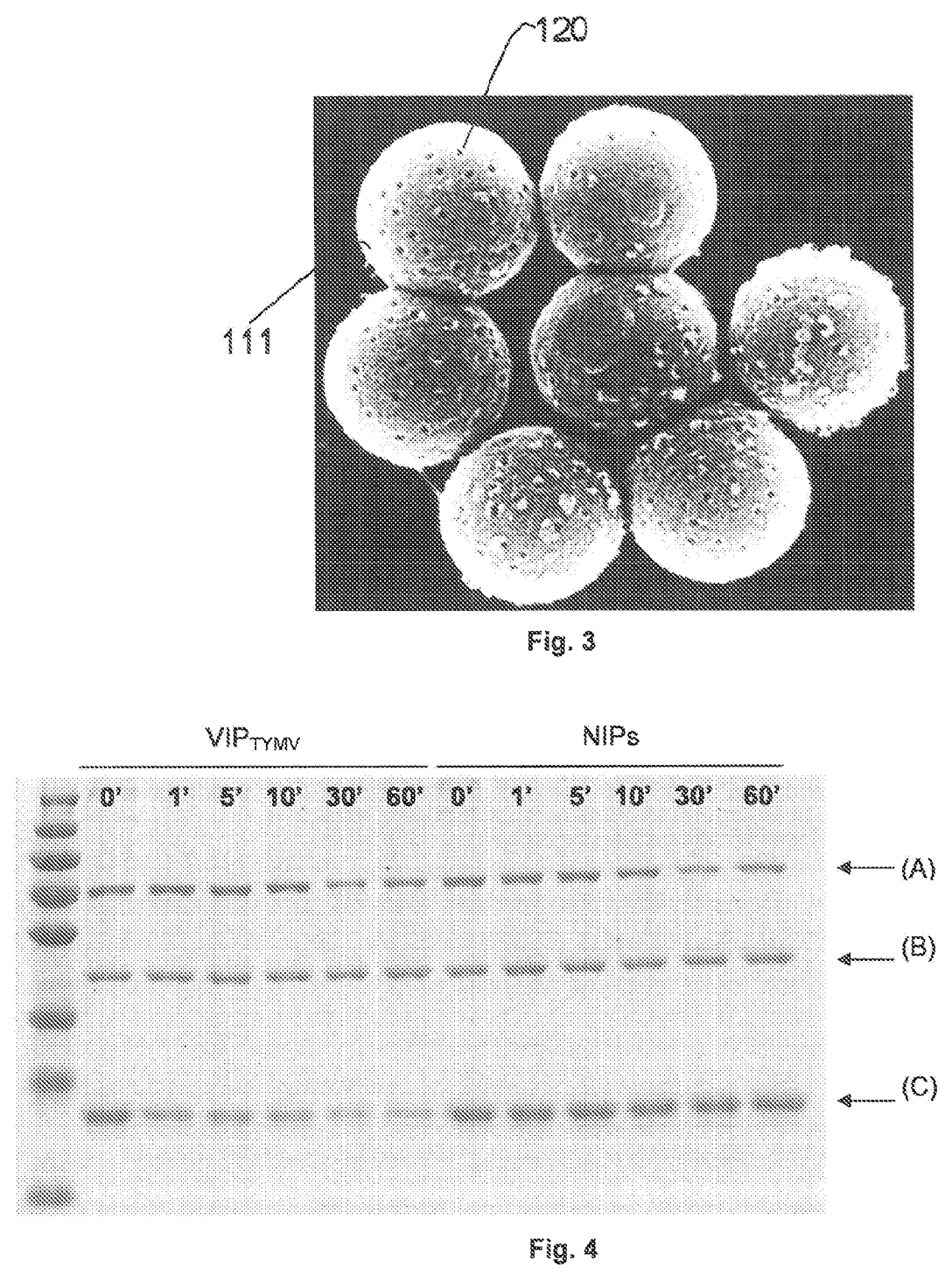

FIG. 3 shows a scanning electron micrograph of virus imprinted particles (VIPs) 111 useable as a molecular recognition element comprising a polymerized recognition material within an embodiment of the method according to the invention. The viruses as templates have been removed and, thus, imprints 120 on a surface of each VIPS have been formed. Each imprint 120 formed in the polymerized recognition material is complementary to a target Within the imprints, there are chemical functional groups specifically oriented such as recognition binding-functions in order to interact with the target.

FIG. 4 shows a representative SDS-PAGE (sodium dodecylsulfate polyacrylamide gel electrophoresis) showing an interaction assay for particle-virus interaction. In the first six lanes on the left hand side of FIG. 4 (0 min to 60 min) supernatants of samples being a mixture of BSA (bovine serum albumine), TBSV (tomato bushy stunt virus: non template virus) and TYMV (turnip yellow mosaic virus: template virus) and being treated with $VIP_{TYMV}$ as recognition element provided according to an embodiment of the inventive method are analyzed. In the second six lanes on the right hand side of FIG. 4 (0 min to 60 min) supernatants of the samples being treated with NIPs (non-imprinted particle) as recognition elements are analyzed. Thereby, the top band A represents BSA as target, the middle band B represents TBSV (non template virus) as target and the bottom band C represents TYMV (template virus) as target. Neither non-template virus (TBSV) nor BSA binds specifically to $VIP_{TYMV}$ or to NIP. In contrast thereto, the template virus TYMV binds specifically to $VIP_{TYMV}$, while it binds non-specifically to the NIPs. Within the first minute of interaction, the template virus TYMV specifically binds to $VIP_{TYMV}$ with most of its initial amount.

Figure 5:
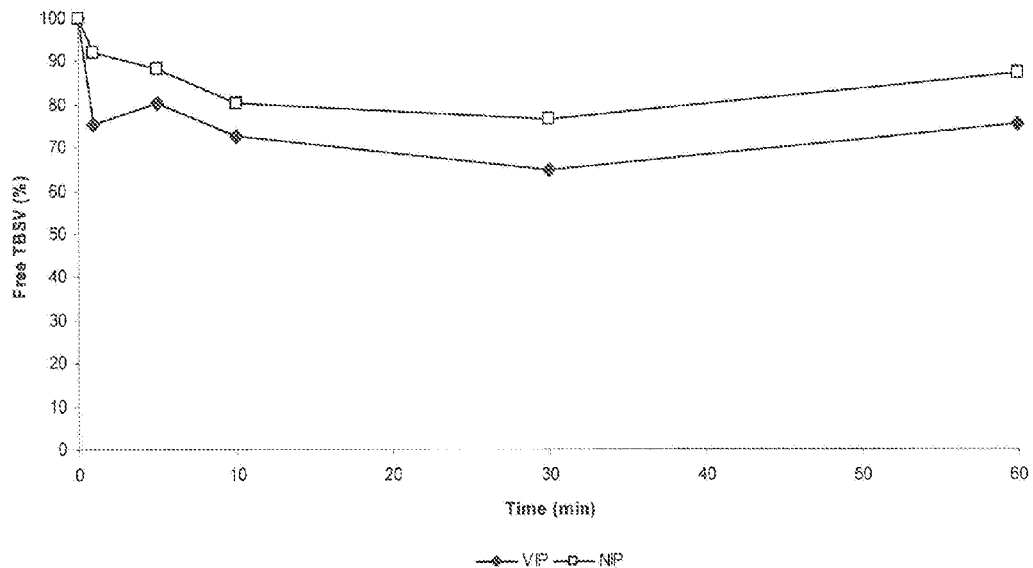
FIG. 5 shows percentages of free TBSV (tomato bushy stunt virus) in function of time in use of the NIPs from FIG. 4 and the VIPs from FIG. 3 for binding the TBSV.

FIG. 5 shows percentages of free TBSV (tomato bushy stunt virus) in function of time for NIP (non-imprinted particle) as recognition element and for VIP (virus imprinted particle) as recognition element provided according to an embodiment of the inventive method. As can be seen in FIG. 5 the use of the VIPs results in a significantly improved binding of the TBSV compared to the use of NIPs. Furthermore, it can be seen in FIG. 5 that most of binding of free TBSV occurs in a comparably short time period regardless of the used recognition element. Starting with a comparably high binding rate in the first two or three minutes, the binding rate does not further improve after about 30 min.

Figure 6:
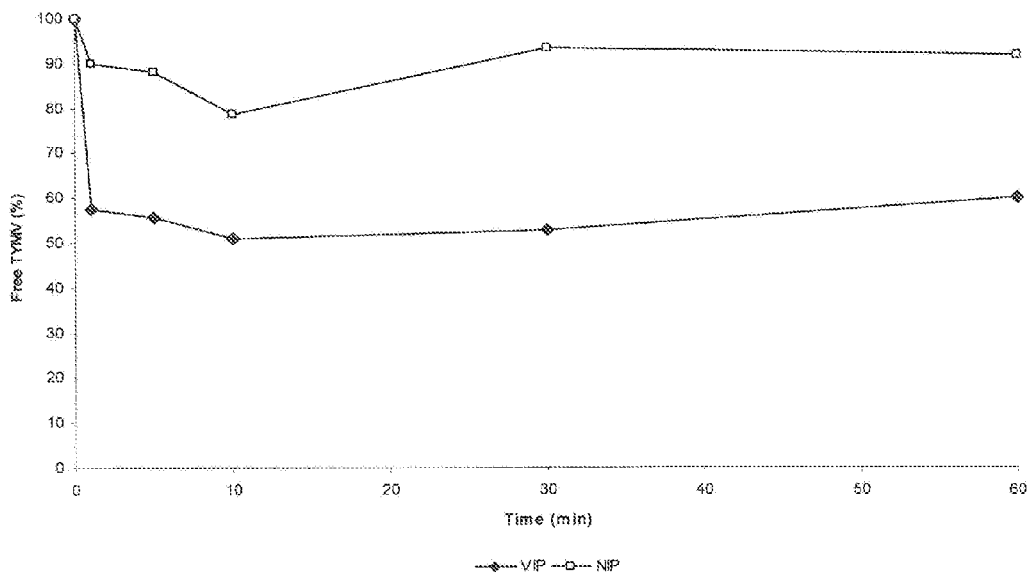
FIG. 6 shows percentages of free TYMV (turnip yellow mosaic virus) in function of time in use of the NIPS from FIG. 4 and the VIPs from FIG. 3 for binding the TYMV.

FIG. 6 shows percentages of free TYMV (turnip yellow mosaic virus) in function of time for NIP (non-imprinted particle) as recognition element and for VIP (virus imprinted particle) as recognition element provided according to an embodiment of the inventive method. As can be seen in FIG. 6 the use of the VIPs results in an even more significantly improved binding of the TYMV compared to the use of NIPs than in FIG. 5. Furthermore, it can also be seen in FIG. 6 that most of the binding of free TYMV occurs in a comparably short time period regardless of the used recognition element. Starting with a comparably high binding rate in the first one or two minutes, the binding rate does not further improve after about 10 min.

Figure 7:
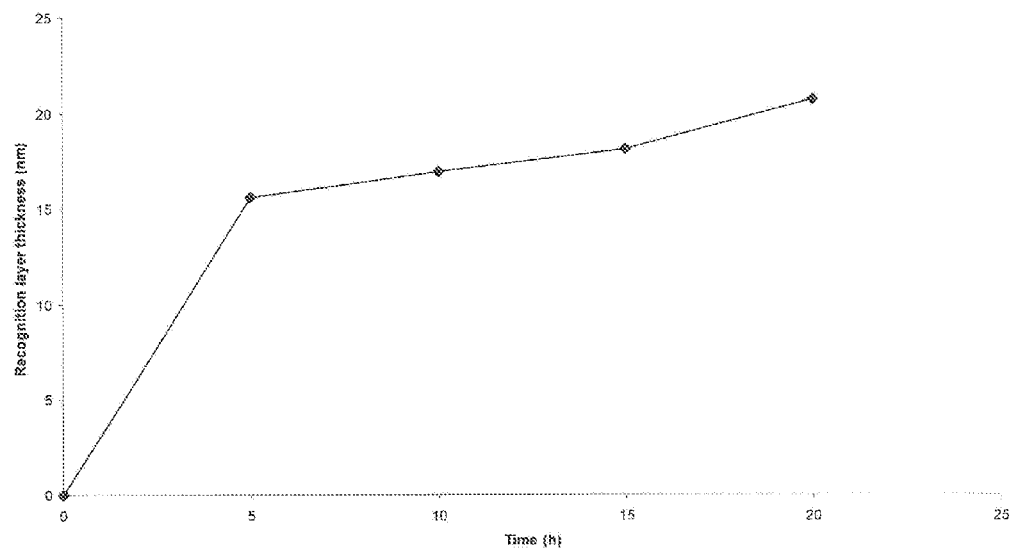
FIG. 7 shows polymerization duration-dependent thicknesses of polymerized recognition materials of VIPs (virus imprinted particles) as other molecular recognition elements provided by a further embodiment of the method according to the invention.

FIG. 7 shows time-dependently measured layer thickness of a VIP (virus imprinted particle) as molecular recognition element comprising a polymerized recognition material provided by an embodiment of the method according to the invention. Therein, BMV (brome mosaic viruses) have been used as templates. For example, if the thickness is comparably low such as 15 nm, then polymerization duration is about five hours. For a higher thickness (for example 20 nm) of the polymerized recognition material, the polymerization duration is about 20 h. Thus, it can be seen in FIG. 7 that the polymerization duration may provide a precise adjustment of the thickness of the polymerized recognition material within an embodiment of the method according to the present invention.

Figure 8:
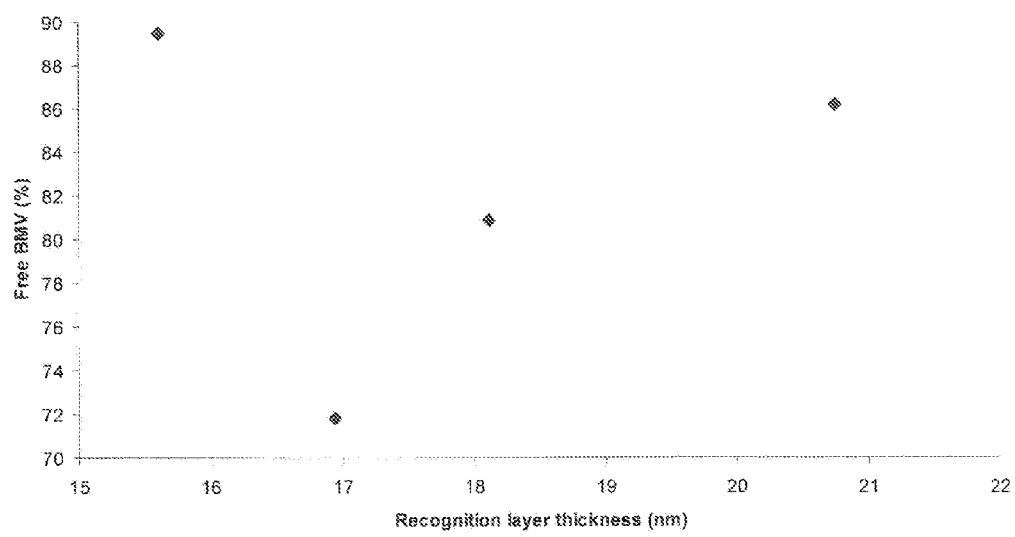
FIG. 8 shows percentages of free BMV (brume mosaic virus) in function of the VIPs from FIG. 7 having different polymerized recognition material thicknesses.

FIG. 8 shows percentages of free BMV (brome mosaic viruses) in function of a layer thickness of a VIP (virus imprinted particle) useable as molecular recognition element provided by an embodiment of the method according to the invention. A thickness of the polymerized recognition material may be adjusted with respect to template and/or target type by determination of an optimal aim thickness of the polymerized recognition material enabling a binding of the respective template and/or target type (e.g. BMV) in an amount according to application's need. For BMV as template and/or target, the optimal aim thickness of the polymerized recognition material is about 17 nm. Thus, it the affinity of the VIP for the target can be adjusted according to application's need via the thickness of the polymerized recognition material.

Figure 9:
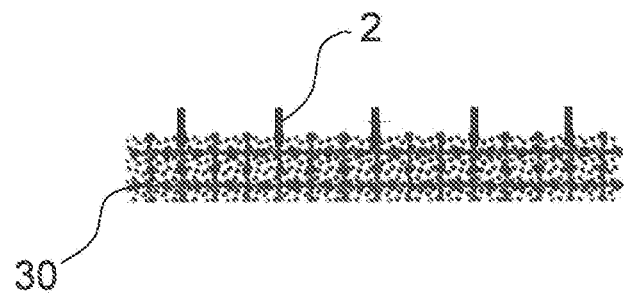
FIG. 9 shows a schematic view of a further carrier material having cross-linkers bound to its surface within another embodiment of the method according to the invention.

FIG. 9 shows a schematic view of a carrier material 30 within an embodiment of the method according to the invention. On a surface of the carrier material 30 cross-linkers 2 are distributed which usable as a linking means. The cross-linkers are homogeneously distributed on the surface of the carrier material 30. Thus, an equal spacing between the cross-linkers 2 is provided which can be a condition for homogeneous binding of templates. The cross-linkers 2 are cross-linking reagents or cross-linkers containing reactive ends to specific functional groups (e.g. primary amines, sulfhydryls, etc.) which bind on one side to the surface of the carrier material 3 and on the other side to a template (see below). For example, a cross-linker 2 can be immobilized on a silica surface as a carrier material 3 and then a template may be bound to an unoccupied binding-site of the cross-linker (see below). Alternatively, the cross-linker 2 can also first bind to the template and then the cross-linker 2 bound to the template binds with its unoccupied binding-site to the surface of the carrier material 3. The cross-linker 2 used within can be chosen according a type of carrier material 3 to be used. For example, the cross-linker 2 can be a cleavable cross-linker, i.e. a cross-linker being capable to cleave its linkage upon external stimuli such as temperature, pH, electricity, light, or a cross-linker such as DTSSP (3,3'-Dithiobis[sulfosuccinimidylpropionate]) being cleavable, for example, by using DTT (Dithiothreitol) as a reducing agent. As a non-limiting example, a silicium surface as a carrier material 3 may be modified with the cross linker 2 bearing a Schiff base bond and linking the silica surface with the template. In case of gold or titan surface as a carrier material 3, a cross-linker 2 can also have a thiol terminus enabling binding to the respective surface and further an intramolecular disulfide bond being cleavable and may link the respective surface with the template.

The following applies to the following description. If in order to clarify the drawings, a figure contains reference signs which are not explained in the directly associated part of the description, then it is referred to previous description sections.

Figure 10:
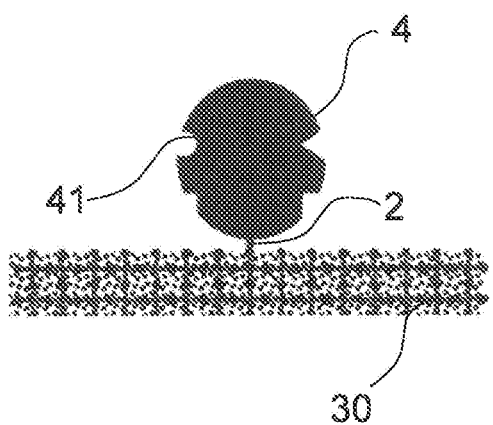
FIG. 10 shows a schematic view of the carrier material from FIG. 9 wherein a virus as a template is bound to the cross-linker.

FIG. 10 shows a virus 4 as a template being bound or immobilized on the surface of the carrier material 30 via one of the cross-linkers 2. The virus 4 comprises binding-sites 41 which are unoccupied.

Figure 11:
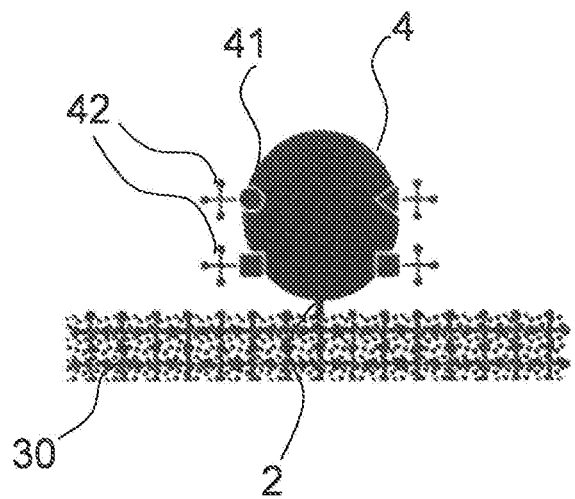
FIG. 11 shows a schematic view of the carrier material from FIG. 10 wherein self-assembled building blocks are provided to the virus.

In FIG. 11 monomeric building blocks 42 complementary to the binding-sites 41 of the virus 4 are provided such that they occupy the binding sites 41 of the virus 4. The building blocks 42 comprise structural monomers and recognition portions. The recognition portions or recognition monomers, respectively, compose structural monomers such as tetraethylorthosilicate (TEOS). The budding blocks 42 can alternatively also be firstly bound to a non-immobilized template which is subsequently immobilized on the carrier material 3. After the building blocks 42 are provided to the virus 4, a liquid monomeric recognition material is provided onto the surface of the carrier material 30. The recognition material is then polymerized for a predefined duration such that a polymerized recognition material having a thickness corresponding to the polymerization duration is formed on the surface of the carrier material 30. Depending on this predefined duration imprints of a correspondingly predefined size are formed in the polymerized recognition material.

Figure 12:
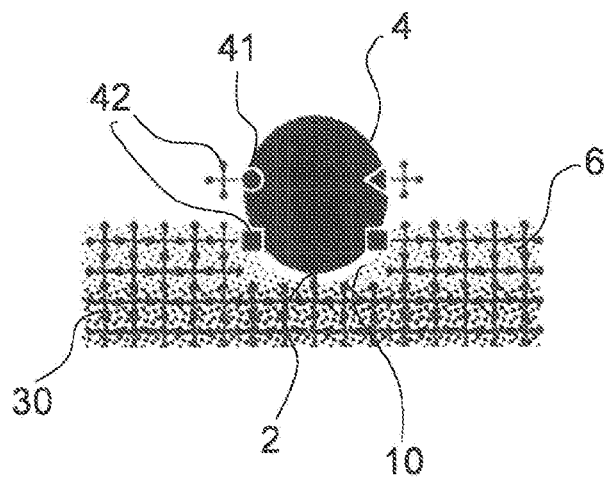
FIG. 12 shows a schematic view of the carrier material from FIG. 11 wherein recognition material of a first thickness is polymerized on the surface of the carrier material.

FIG. 12 shows an embodiment of a polymerized recognition material 6 being built on the surface of the carrier material 30 after a first predefined polymerization duration. The polymerized recognition material 6 has an imprint 10 induced by the virus 4. The size (e.g. diameter, form) of the imprint 10 depends on the virus 4 size and the thickness of the polymerized recognition material 6. Also the amount of binding-functions built by building blocks 42 integrated in the polymerized recognition material depends on the thickness of the polymerized recognition material 6. The virus 4 is then released from the imprint 10 of the polymerized recognition material 6. Preferably, such release of the virus 4 is performed in a gentle way, meaning that the released virus 4 can be re-used. Such a gentle release of the virus 4 may be achieved by breaking the binding between the template and the carrier material 30.

Figure 13:
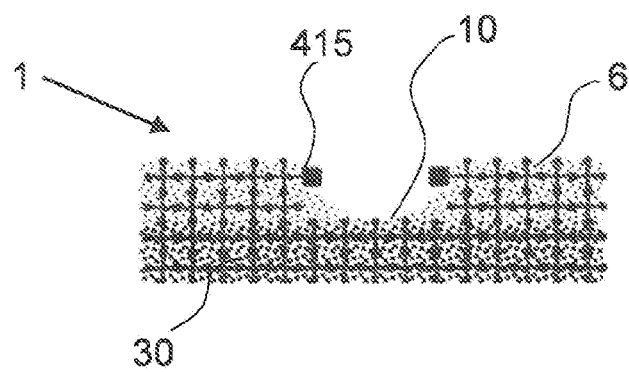
FIG. 13 shows a first molecular recognition element provided by the method from FIG. 9.

In FIG. 13 an embodiment of a molecular recognition element 1 with the polymerized recognition material 6 is shown. As shown in FIG. 13, the thickness of the polymerized recognition material is comparably small due to the comparably short first polymerization duration. Consequently, the size of the imprint 10 is comparably small and the amount of binding-functions 415 is comparably low. Since the affinity of the polymerized recognition material 6 to a target depends on the size of the imprint 10 and on the amount of binding-functions 415, the affinity of the molecular recognition element 1 is comparably low. Such low-affinity molecular recognition elements 1 are preferred in many possible applications.

Figure 14:
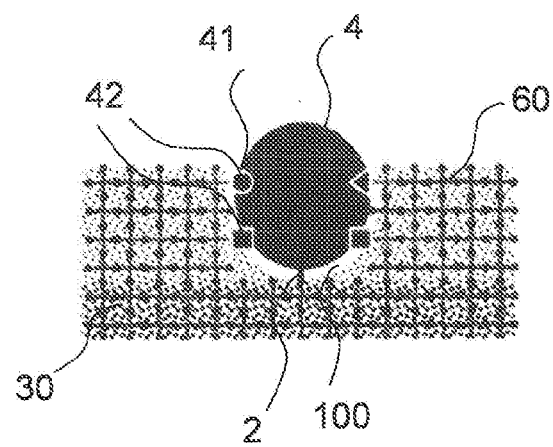
FIG. 14 shows a schematic view of the carrier material from FIG. 11 wherein recognition material of a second thickness is polymerized on the surface of the carrier material as an alternative to the thickness shown in FIG. 12.

FIG. 14 shows another embodiment of a polymerized recognition material 60 being built on the surface of the carrier material 30 after a second predefined polymerization duration. The polymerized recognition material 60 has an imprint 100 induced by the virus 4. The size of the imprint 100 also depends on the virus 4 size and the thickness of the polymerized recognition material 60. Also the amount of binding-functions built by building blocks 42 integrated in the polymerized recognition material depends on the thickness of the polymerized recognition material 6. The virus 4 is again then released from the imprint 100 of the polymerized recognition material 60.

Figure 15:
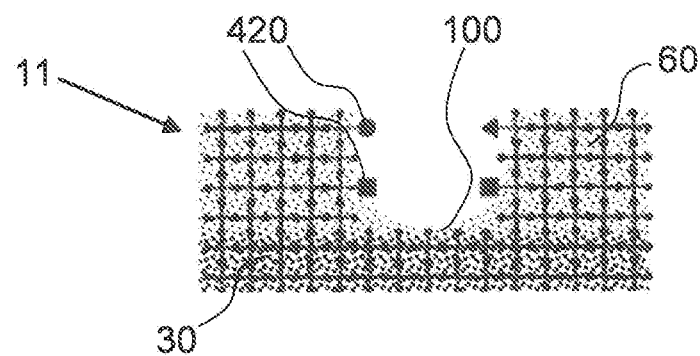
FIG. 15 shows a second molecular recognition element provided by the method from FIG. 9.

In FIG. 15 another embodiment of a molecular recognition element 11 with the polymerized recognition material 60 is shown. As shown in FIG. 15, the thickness of the polymerized recognition material is comparably large due to the comparably long second polymerization duration. Consequently, the size of the imprint 100 is comparably large and the amount of binding-functions 420 is comparably high. Since the affinity of the polymerized recognition material 60 to a target depends on the size of the imprint 100 and on the amount of binding functions 420, the affinity of the molecular recognition element 1 is comparably high. Such high-affinity molecular recognition elements 1 are also preferred in many possible applications.

The foregoing description will be more fully understood with reference to the following Examples. Such Examples, are, however, exemplary of methods of practicing the present invention and are not intended to limit the scope of the invention.

The following Examples illustrate the invention.

Example 1

Specific Molecular Recognition of Plant Viruses

Virus imprinted particles (VIPs) are produced in a three steps process, involving covalent anchoring of the viral particles on the surface of silica nanoparticles (SNP), grown of an ultra-thin layer of silica (<20 nm) on the so-produced particles (400 nm) in water and removal of template virus, wherein each produced particle has an overall particle size of 440 nm (400 nm+(20 nm×2)=440 nm).

Silica Nanoparticles Synthesis

SNPs are synthesized using the well known Stöber method adapted from A. Imhof et al. (J. Phys. Chem. B, 1999, 103, 1408). In a 1 L round bottom flask are added: ethanol (345.4 mL), ammonia 25% (39.3 mL) and TEOS (tetraethylorthosilicate, 15.3 µL) The reaction mixture is kept under stirring (600 rpm) for 24 h at a constant temperature (20° C.). In FIG. 1 is given a representative picture of the produced nanoparticles.

Virus Immobilization.

SNPs are first surface modified with APTES (3-aminopropyltriethoxysilane). Under magnetic stirring, 10 µL of APTES are added to 10 mL of an aqueous suspension of SNPs at a concentration of 3 mg/mL. After 30 min of reaction, the particles are washed. The so-produced amino modified particles are then reacted with an excess of glutaraldehyde at a final concentration of 1% for 1 h under stirring condition (400 rpm) in order to enable a binding of the template to the particle-modified surface. After washing, a solution of turnip yellow mosaic virus (TYMV) is added at a final concentration of 75 µg/mL. The reaction mixture is kept under stirring for 1 h. Thus, the template (i.e. TYMV) is bound to the particle surface (FIG. 10).

Alternatively, the cross-linker (i.e. APTES, glutaraldehyde) may first bind to the template and then the cross-linker bound by the template may bind with its unoccupied binding-site to the silica surface of the particle. The crosslinker as used herein may depend on type of carrier material to be used. Preferably, the crosslinker may be a cleavable crosslinker, i.e. a crosslinker being capable to cleave its linkage upon external stimuli such as temperature, pH, electricity, light, or a crosslinker such as DTSSP (3,3'-Dithiobis[sulfosuccinimidylpropionate]) being cleavable, for example, by using DTT (Dithiothreitol) as a reducing agent. As a non-limiting example, a silica surface as a carrier material may be modified with a cross-linker bearing a Schiff base bond and linking the silica surface with the template.

Recognition Layer Growth.

In order to assess the layer growth kinetics, at 10° C., to a suspension of virus-modified SNPs are added 10 mL of TEOS (=structural building block (monomers)) and the mixture kept under stirring. After 2 hours a specific mixture of "recognition" building blocks (monomers) are added (Hydroxymethyltriethoxysilane, HMTEOS, 5 µL; Benzyltriethoxysilane, BTES, 5 µL: n-Propyltriethoxysilane, PTES, 5 µL; and APTES, 5 µL) (FIG. 11). Growth of recognition material on silica surface is stopped via double water wash when an aim thickness of the grown recognition material is essentially equalised. For example, when the grown recognition material should possess a low-affinity property for binding template or target, the aim thickness is lower than half of diameter of the template (FIG. 12), i.e. for a template-virus such as Turnip Yellow Mosaic Virus (TYMV) having a diameter of about 28 nm, the aim thickness of a low-affinity recognition material is in a range of 1% to 10%. of the diameter of the template.

When a grown recognition material should possess a middle-affinity property for binding template or target, the aim thickness is middle (FIG. 14), i.e. for a template-virus such as Turnip Yellow Mosaic Virus (TYMV) having a diameter of 28 nm, the aim thickness of a high-affinity recognition material is in a range of 30% to 45% of the diameter of the template.

When a grown recognition material should possess a high-affinity property for binding template or target, the aim thickness is high (FIG. 14), i.e. for a template-virus such as Turnip Yellow Mosaic Virus (TYMV) having a diameter of 28 nm, the aim thickness of a high-affinity recognition material is in a range of 45% to 50% of the diameter of the template.

Selected samples are analyzed using scanning electron microscope (Zeiss, SUPRA 40 VP) and the acquired pictures are used for particles size measurement using the Analysis® (Olympus) software package (~100 measurements per sample).

In FIG. 2 is given the measured layer growth over duration. It has to be noted that the measured kinetic is dependant on the composition of the reaction mixture and the reaction conditions.

In order to passivate the non-imprinted surfaces, the so-produced VIPs (10 mL, 3 mg/mL) are incubated for 2 hours with 40 µl of PEOTMS (2-[methoxy(polyethyleneoxy)propyl)]trimethoxysilane__6 to 9 ethyleneoxide units) under stirring. VIPs are then washed twice with water. As the viruses are still present into the cavities, the surface of the binding sites is not accessible to the modification that will only modify chemically the non-imprinted areas of the carrier material. The oligo-ethyleneglycol chains will moderate non-specific adsorption at the surface of the carrier material.

Removal of the Template Virus.

The removal of the virus is carried out incubating the VIPs at room temperature for 30 min in the removal buffer (RB, 1 M HCl, 0.1% Triton-X 100) under stirring and submitting the mixture to ultrasonic treatment for additional 15 min The so-produced VIPs are then analyzed by SEM, a representative micrograph is given in FIG. 3, FIGS. 13 and 15 illustrate a low- and high-affinity recognition material, respectively, wherein the template has been removed. Alternatively, release of the template can be in a gentle way, meaning that the released template is not impaired and, thus, the released template may be reused for preparation of a further molecular recognition element Such a "gentle release of the template" may be achieved by breaking the binding between the template and the carrier material which may be accomplished by using reversible chemical reactions such as breaking of a Schiff base using acidic treatment, reduction or oxidation of disulfide bond, or using cleavable cross-linkers, i.e. DTSSP (3,3'-Dithiobis[sulfosuccinimidylpropionate]) being cleavable, for example, by using DTT (Dithiothreitol) as a reducing agent.

Particles-Virus Interaction

A suspension of VIPs at a concentration of 1.7 mg/mL is incubated at 25° C. under shaking (500 rpm) for increasing reaction durations with a mixture of BSA (bovine serum albumin), TBSV (tomato bushy stunt virus, non-template virus) and TYMV (template virus). Non-imprinted particles are used a references. The non imprinted particles (NIP) have been produced following the same procedure as the VIPs without addition of virus.

Samples are collected at 1, 5, 10, 30 and 60 minutes after the interaction and centrifuged in order to pellet down the particles. Supernatants are collected for protein analysis using SDS PAGE (sodium dodecylsulfate polyacrylamide gel electrophoresis). The obtained gels are scanned and the intensity bands are detected using an analysis software, such as Quantity One® (Bio-Rad).

In FIGS. 5 and 6 are given the quantification of the free TBSV and TYMV, respectively. From these results, it is evident that there is no relevant difference between the VIP and the NIP with regard to the non-template virus (TBSV). The same result is observed for BSA (not shown). In contrast to BSA and TBSV, the template virus TYMV binds specifically to VIPs. While it binds non-specifically to the NIPs. Within the first minute of interaction, the template virus-TYMV, specifically binds to the VIP, almost to 50% of its initial amount and this value remains constant.

Example 2

Tunable Affinity for Plant Viruses

The virus imprinted particles (VIPs) are produced following the same procedure than in Example 1, using brome mosaic virus (BMV) as template (VIPBMV).

An aqueous solution of BMV with a concentration of 250 µg/mL is incubated with $VIP_{BMV}$ having increasing recognition layer thickness at a concentration of 5 mg/mL at 25° C. under shaking (500 rpm). In FIG. 7 is given the measured layer growth over duration of the VIP used in this experiment. Samples are collected after 60 minutes of interaction and centrifuged in order to pellet down the particles. Supernatants are collected for protein measurements using Agilent 2100 Bioanalyzer. In FIG. 8 is given the quantification of the free BMV in relation with the recognition layer thickness. From these results, is possible to see a clear correlation between the affinity of the VIPs for their target (i.e. template virus) and the thickness of the grown layer. Indeed, when the layer thickness is greater than the radius of the virus (>17 nm), imprints are less accessible to the virus, due to the burying of the virus during the layer growth. While with layers with too low recognition thickness, imprints are not deep enough and the contact between the virus and the imprint is not enough to allow a stable binding. The recognition layer thickness is intimately related with affinity/specificity of the so produced VIPs. The ability to finely control this step (temperature, silanes composition) provides a method to produce tunable affinity nanomaterials for their target (bio) molecule.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figures individually although they may not have been described in the afore or following description. Furthermore, in the claims the word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

While the invention has been illustrated and described in detail in the drawings and foregoing description, such illustration and description are to be considered illustrative or exemplary and not restrictive. It will be understood that changes and modifications may be made by those of ordinary skill within the scope and spirit of the following claims. In particular, the present invention covers further embodiments with any combination of features from different embodiments described above and below.

The invention also covers all further features shown in the Figures individually although they may not have been described in the afore or following description. Furthermore, in the claims the word "comprising" does not exclude other elements or steps, and the indefinite article "a" or "an" does not exclude a plurality. A single step may fulfil the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The invention claimed is:

1. A method for preparation of a molecular recognition element (1, 11, 111) comprising the steps of binding a template (4) to a surface of a carrier material (3, 30), providing a recognition material to the surface of the carrier material (3, 30),
    initiating polymerization of the recognition material on the surface of the carrier material (3, 30), stopping the polymerization of the recognition material on the surface of the carrier material (3, 30), and releasing the template (4) from the surface of the carrier material (3, 30) and the polymerized recognition material (6, 60), characterized in that an aim size of individual imprints (10, 100, 120) is predefined, and the polymerization of the recognition material on the surface of the carrier material (3, 30) is stopped when a size of individual imprints (10, 100, 120) of the polymerized recognition material (6, 60) essentially equals to the predefined aim size.

2. The method according to claim 1, wherein predefining the aim size comprises predefining an aim thickness, wherein the polymerization of the recognition material on the surface of the carrier material (3, 30) is stopped when a thickness of the polymerized recognition material (6, 60) essentially equals to the predefined aim thickness.

3. The method according to claim 2, wherein predefining the aim thickness comprises predefining an aim polymerization duration under given conditions and wherein the polymerization of the recognition material on the surface of the carrier material (3, 30) is performed under the given conditions and stopped when a duration of the polymerization of the recognition material on the surface of the carrier material (3, 30) essentially equals to the predefined aim polymerization duration.

4. The method according to claim 2, wherein the template (4) is a virus or a structural analogue of a virus and the aim thickness is within a range of about 1% to about 50% of a diameter of the template (4).

5. The method according to claim 1, comprising the step of activating the surface of the carrier material (3, 30) prior binding the template (4) to the surface of the carrier material (3, 30), wherein a linking means (2) is homogeneously distributed on the surface of the carrier material (3, 30).

6. The method according to claim 1, comprising the step of providing building blocks (42, 415, 420) complementary to the template (4) prior initiating polymerization of the recognition material on the surface of the carrier material (3, 30).

7. The method according to claim 6, comprising the steps of analysing a surface structure of the template (4) or of a target prior providing the building blocks (42, 415, 420), and choosing the building blocks (42, 415, 420) corresponding to the surface structure.

8. The method according to claim 1, wherein an outer surface of the polymerized recognition material (6, 60) being opposed to the carrier material (3, 30) is passivated prior the template (4) being released from the surface of the carrier material (3, 30) and the polymerized recognition material (6, 60).

9. The method according to claim 8, wherein passivating the outer surface of the polymerized recognition material (6, 60) comprises chemical and/or physical and/or biochemical modification of the outer surface of the polymerized recognition material (6, 60) on the surface of the carrier material (3, 30).

10. The method according to claim 1, wherein releasing the template (4) from the surface of the carrier material (3, 30) and the polymerized recognition material (6, 60) comprises breaking the binding between the template (4) and the carrier material (3, 30) without impairing the template.

11. The method according to claim 1, wherein the binding of the template (4) to the surface of the carrier material (3, 30) is covalent binding.

12. The method according to claim 1, wherein the template (4) is selected from a group consisting of supramolecular complexes, viruses, peptides, proteins, polymeric nanoparticles, inorganic nanoparticles, prokaryotic cells, eukaryotic cells, plant cells and derivatives thereof.

13. The method according to claim 1, wherein the carrier material (3, 30) is selected from a group consisting of silicon oxides, titanium oxides, organic, inorganic, polymeric or inorganic-organic composites and self-assembled organic material.

* * * * *